United States Patent [19]

Hirschman

[11] 4,095,542
[45] Jun. 20, 1978

[54] METHODS OF MAKING FEMININE HYGIENIC PADS

[76] Inventor: Shalom Z. Hirschman, 110-11 Queens Blvd., Forest Hills, N.Y. 11375

[21] Appl. No.: 732,941

[22] Filed: Oct. 15, 1976

[51] Int. Cl.² ............................................. A61F 13/18
[52] U.S. Cl. ................................... 112/262; 128/270; 128/285; 128/290 P
[58] Field of Search ............ 128/285, 270, 295, 290 P; 112/262

[56] References Cited

U.S. PATENT DOCUMENTS

| | | | |
|---|---|---|---|
| 1,742,830 | 1/1930 | Seaman et al. | 112/262 X |
| 2,598,638 | 5/1952 | Enos | 112/262 X |
| 3,094,083 | 6/1963 | Weeks | 112/262 |
| 3,359,981 | 12/1967 | Hochstrasser | 128/285 |
| 3,726,277 | 4/1973 | Hirschman | 128/285 |
| 3,983,873 | 10/1976 | Hirschman | 128/285 |

*Primary Examiner*—Alfred R. Guest

*Attorney, Agent, or Firm*—Irving Seidman

[57] ABSTRACT

Methods of making feminine hygienic pads from non-layered and layered material by use of folding to make predetermined multiple folds in said material, said folding may be with a device attached to a sewing machine for stitching said pads longitudinally adjacent a longitudinal leading edge creating an anterior narrow leading panel of narrow thickness and a posterior under panel of a wider thickness providing a long geometric form. Thereafter the said long geometric form is multiple cut providing pads of about two inches long. In some pads having fillers, the filler material is laid between the folds of the layered or non-layered material prior to stitching and after the long geometric form is produced, it is cut into desired lengths about two inches long providing the pads. These pads are for insertion into the interlabial space and have a geometric configuration which facilitates insertion of the pad into the interlabial space and has improved retention within such space.

16 Claims, 20 Drawing Figures

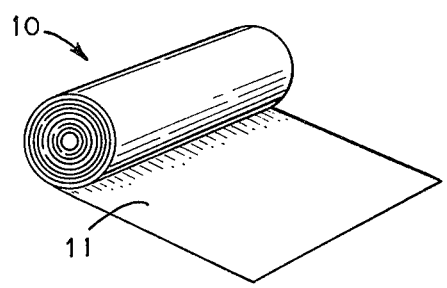
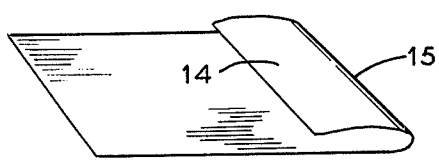
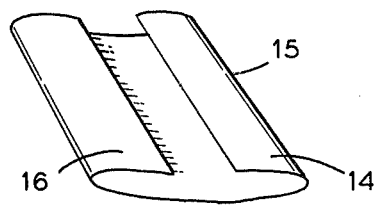
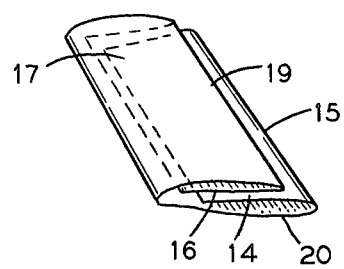
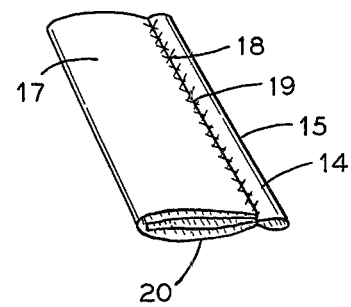
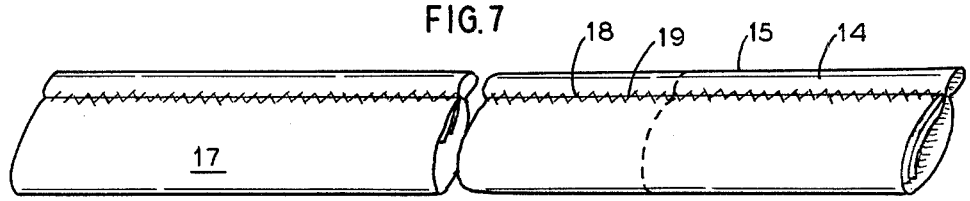
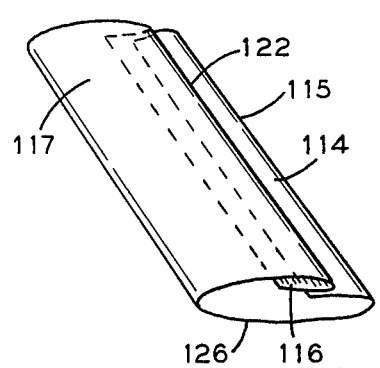
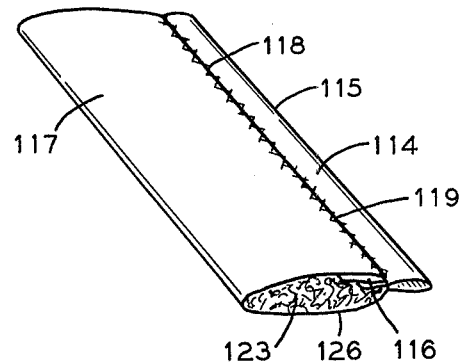

METHODS OF MAKING FEMININE HYGIENIC PADS

BACKGROUND OF THE INVENTION

Applicant has created a number of feminine hygienic pads for use by females to absorb uncontrolled discharges, such as urine, vaginal secretions, postcoital leakage, menstrual straining, or the like as shown in his U.S. Pat. Nos. 3,726,277 and 3,983,873.

Such pads must be carefully made of certain soft layered or non-layered materials and in some versions with filler materials so that certain dimensions of the pads are maintained. Such pads have been difficult and relatively expensive to produce.

An object of this invention is to provide a method, or methods of producing such pads inexpensively maintaining desired dimensions and characteristics of the pad so that the female may place such pad into the interlabial space easily and quickly to absorb uncontrolled discharges such as urine or the like.

The methods used to create such pads must provide an inexpensive pad having certain geometric cross sections distinguished by anterior leading edge portions of reduced transverse thickness and posterior portions of greater or more substantial transverse thickness and the desired dimensions and geometric configuration must be substantially maintained during quantity production. The methods of applicant accomplishes such objects and results.

Other objects of this invention will in part be obvious and in part hereinafter pointed out.

DESCRIPTION OF THE DRAWINGS

FIG. 1 is a perspective view of a roll of layered material used in the making of the hygienic pads;

FIG. 2 is an enlarged sectional view of a four layered material of the roll of material shown in FIG. 1;

FIG. 3 is a perspective view of one fold of the layered material;

FIG. 4 is a perspective view of another fold of the layered material;

FIG. 5 is a perspective view of the folded material folded upon itself leaving a longitudinal narrow panel and leading edge;

FIG. 6 is a perspective view of the folded material shown in FIG. 5 stitched adjacent its leading edge creating the complete geometric form of the first version of the pad;

FIG. 7 is a perspective view of a long pad after folding and stitching but before it is cut into the desired pad lengths;

FIG. 8 is a perspective view of another or second form of the material showing the manner of folding such material during the method of making the pad;

FIG. 9 is a perspective view of the material folded in four panels, shown in FIG. 8, wrapped around a filler and stitched and finished as a pad;

DESCRIPTION OF THE PREFERRED METHODS

Figure 10:
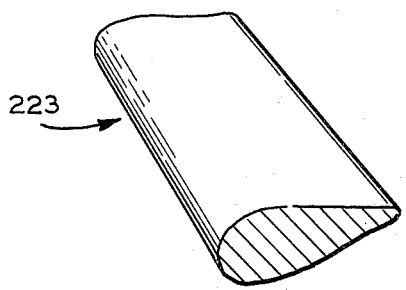
FIG. 10 is a perspective view of a pre-shaped pad of pressed material used as an inner core for a pad.

In the first method of making hygienic pads, a flat piece of material comes off a roll 10 or a folded bale generally commercially made about forty-two or sixty inches wide; however, such rolls of material may be made in any widths desired. The material is then cut to about 2¼ inches wide, as shown in FIG. 1. Two methods of cutting may be used, namely material of roll 10 may be cut laterally from the material as it is unrolled, or longitudinally through the roll. The material 11 of roll 10 is preferably comprised of a four or eight plies of suitable cotton gauze, synthetic material, or blend of cotton and cellulose fibers, as shown in FIG. 2. The flat material 11 may be of a suitable thickness, such as 1.5 of 1/32 inch for four ply and 3/32 inch for eight ply material with an outer layer of cotton gauze 12 and inner layers 13 of pressed cotton, or other cellulose fibers as shown in FIG. 2.

The steps of the method consist of folding the material along its right longitudinal end about ⅜ inch, as shown in FIG. 3 to create a panel 14 and an anterior leading edge 15. Another fold is made at the left longitudinal and about ½ of an inch wide, as shown in FIG. 4, to create the first part of the outer panel or body 16. The panel 16 and the material beneath it is folded over again to provide the posterior panel or portion 17, as shown in FIG. 5. A folding attachment (not shown) associated with a sewing machine makes the folds hereinbefore described automatically. Such folding attachments for sewing machines are known in the art and a special attachment for the special dimensions and number of folds desired can be readily made. Simultaneously, as the material is folded prior to being fed beneath the presser foot of the sewing machine (not shown), the material 14, 16, 17, and 20 is stitched with a fine continuous zig-zag stitching line 18 about ⅛ inch from the leading edge 15 to fasten the edge 19 of the posterior portion or panel 17 to panel 14, thus creating the fixed anterior leading edge 15 about ⅛ inch in width to complete the geometric form as shown in FIG. 6. Since the material used is taken from the roll of material 10, shown in FIG. 1, the folded and stitched unit consists of a long pad, as shown in FIG. 7 which is then cut into the small pads of the desired size, preferably of about two inches in length, as shown in FIG. 6. These short pads, shown in FIG. 6, are then ready for further processing and eventual packing for delivery to the distributors.

In another method of folding the material, the panel 14 is created by folding the material along its right longitudinal end about ⅜ of an inch, as shown in FIG. 3, but the panel 16 is created by making a fold at the left longitudinal end about 1 inch wide. The panel 16 and the material beneath it is folded over again upon itself to provide the posterior postion 17 which now is comprised of five filler panels instead of the four filler panels shown in FIGS. 5 and 6.

Pads of varying numbers of filler panels in the posterior portion 17 can be created by varying the numbers of folds along the right longitudinal end and the left longitudinal end of the material. For example, a pad with six filler panels in the posterior portion 17 can be created by folding the left longitudinal end of the material 1¼ inches and folding over again on itself to create a panel ⅝ of an inch wide. The right longitudinal end is folded as described in FIGS. 4 and 5 to provide a posterior portion 17 with six filler panels.

The widths of the fold made along the right and the left longitudinal ends of the material can also be varied to create pads with various numbers of filler panels and varying curvilinear and planar cross-sections.

Figure 13:
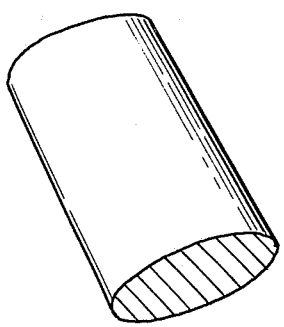
FIGS. 13 and 14 are perspective views of other pre-shaped pads of pressed material that may be used as inner cores for the pad in place of the core shown in FIG. 10.

In a second form of the pad, the folding process of making the same is shown in the steps illustrated in FIGS. 8 and 9. The material comes commercially in a roll similar to roll 10 and may be folded over pressed cotton or cellulose filler 123 to increase the absorptive capacity of the pad. In such form, shown in FIG. 9, where the filler material is used, the cotton gauze material 11 may have fewer layers of the fiber so that the resultant pad is not too thick. Thus, the material and method used for making such interlabial feminine hygienic pads is similar to the first method above described, except that a filler 123 is introduced into the material as it is being automatically folded and before the material is stitched together. The filler may be absorbent or pressed cotton, cellulose, viscose, or similar fibers and may be preferably of an egg shaped cross section, as shown in FIG. 10, or oval, as shown in FIG. 13.

In this second form, as best shown in FIG. 8, the material 11 is about 1⅝ inches wide. The material 11 is folded along its right longitudinal end about ¼ inch creating a panel 114 and an anterior leading edge 115. At the left end, a fold 122 is made about ⅛ inch in width from fold 122 to create the underneath panel 116 as the part of the outer or posterior panel or body 117. The filler material 123, in the form of a ribbon, is fed onto the panel 126, which is only part of the posterior portion, just before the outer or posterior panel 117 with its underneath panel 116 is folded over the filler 123 and the opposite outer or posterior panel 126 and is then stitched with a fine continuous zig-zag stitching line 118 about ⅛ inch from the leading edge 115 thus fastening the edge 119 of posterior portion to panel 114 and creating the anterior leading panel 114 and edge 115 to complete the geometric form shown in FIG. 9. The long pad with the filler therein, of which FIG. 9 shows a small portion, is cut in about two inch lengths and is about ⅝ of an inch in width and comprises the finished interlabial feminine hygienic pad. These pads are packed in desired containers for delivery to distributors.

Figure 11:
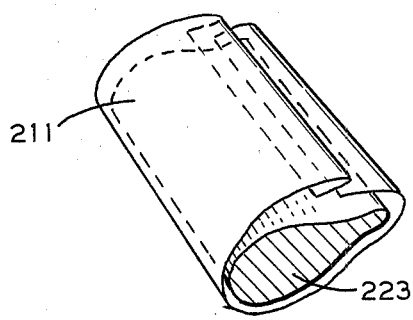
FIG. 11 is a perspective view of the core shown in FIG. 10 with a folded material wrapped around the core prior to stitching.
Figure 12:
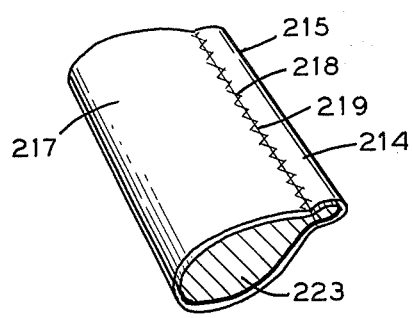
FIG. 12 is a perspective view of the core and the outer folded material shown in FIG. 13 stitched and finished as a pad.
Figure 14:
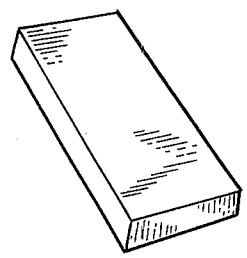

It is within the scope of this invention to use a preshaped pad made from pressed cotton, cellulose, or like material which is wrapped with a gauze material. In FIGS. 10, 13 and 14 there are shown pre-shaped pressed cotton or cellulose inner core forms that may have cotton gauze material 211 wrapped around the form 223 shown in FIG. 10 and in its wrapped form as shown in FIG. 11 which may be called the third form of the invention. This form is then machine stitched by stitching 218 along the edge 219 of the posterior portion or panel 217 about ⅛ inch from the anterior leading edge 215 creating a narrow leading thin panel 214. Instead of using form 223, such pre-shaped forms as shown in FIGS. 13 and 14 may be used. The material that wraps around the inner core, such as 223, is about 1⅝ inches in width. The first left fold is about ⅛ of an inch wide, the next outer adjacent portion is about ½ of an inch, the outer portion falling below the opposite outer portion is about ⅝ of an inch wide and the last right fold is about ¼ of an inch in width. The pad is about 3/8 of an inch thick, about ⅝ of an inch wide and about 2 inches long. The length of the inner cores shown in FIGS. 10, 13 and 14 are preferably of the same length as the outer gauze wrapping. The long geometric form, hereinbefore described is cut into lengths of about 2 inches.

Figure 15:
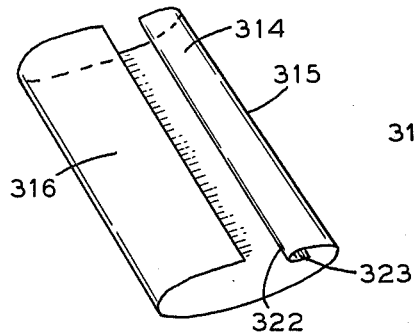
FIG. 15 is a perspective view of the fourth form of the material showing the manner of folding such material during the method of making the pad.
Figure 16:
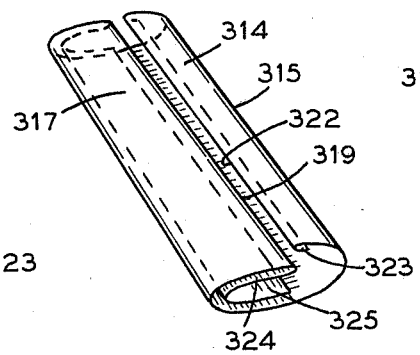
FIG. 16 is a perspective view of the material as the next step of the folding operation.
Figure 17:
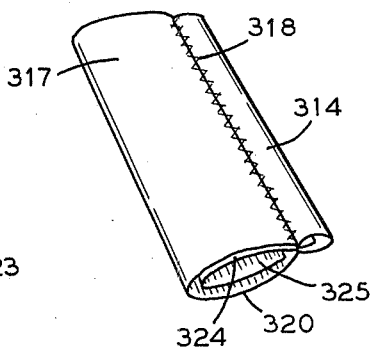
FIG. 17 is a perspective view of the folded material of FIG. 16 stitched together at its abuting edges and through the pad creating the complete geometric form of the fourth version of the pad.

In FIGS. 15, 16 and 17, a fourth form of the pad is shown which is made by folding under the material 11, which is about 2 5/16 inches wide, along its right longitudinal end about 1/16 of an inch in width to create a folded very narrow inner panel 323. The material at the right end is again folded forming a longitudinal anterior narrow panel 314 having an edge 322 and an outer leading edge 315. Panel 323 underlies panel 314. Another fold is made at the left longitudinal end about one inch in width, as shown in FIG. 15 to create the first part of the outer panel or body 316. The panel 316 and the material beneath it is folded over again upon itself to provide the posterior panel or portion 317, as shown in FIGS. 16 and 17, creating a leading edge 319 with two longitudinal panels 324 and 325 beneath the posterior panel 317.

Edges 319 and 322 are positioned so that they abut one another. A fine continuous longitudinal stitching line 318, preferably of the zig-zag type, is made through the material, as shown in FIG. 17, joining the two abutting edges 319 and 322 together creating the stitched anterior narrow leading panel 314 with its leading edge 315 and its filler panels 324 and 325 between its posterior portions 317 and 320, and the narrow panel 314, as shown in FIG. 17.

Figure 18:
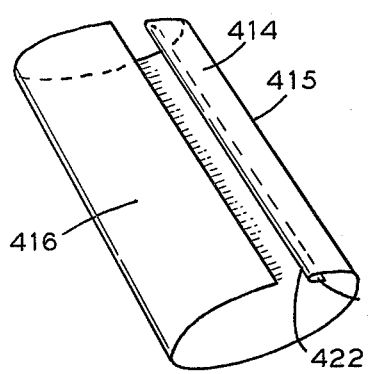
FIG. 18 is a perspective view of the fifth form of the material showing the manner of folding such material during the making of this pad.
Figure 19:
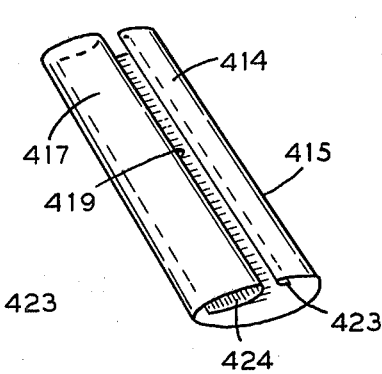
FIG. 19 is a perspective view of the material as the next step of the folding operation.
Figure 20:
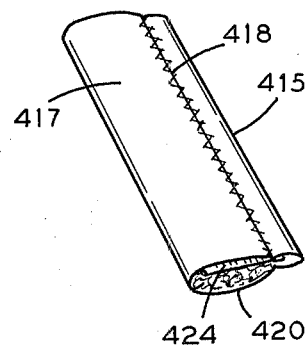
FIG. 20 is a perspective view of the folded material of FIG. 19 stitched together at its abuting edges and through the pad creating the complete geometric form of the fifth version of the pad.

In FIGS. 18, 19 and 20, a fifth form of the pad is shown which is similar in all respects to the fourth form shown in FIGS. 15, 16 and 17, except that the panel 325 is eliminated. This method is suited for wrapping around a filler as shown in FIGS. 8 through 14. All the parts are numbered in a similar manner to the parts shown in FIGS. 15, 16 and 17 except that such parts bear the numbers in the 400's instead of the 300's. The width of the material 11 used in the fifth form is about 1 13/16 of an inch instead of 2 5/16 of an inch used in the fourth form of the pad shown in FIGS. 15, 16 and 17. Panel 423 is about 1/16 of an inch in width, panel 414 is about ⅛ of an inch in width and panel 416 is about ½ of an inch in width. The total width of the finished pad, as shown in FIG. 20 is about ⅝ of an inch and the length is about two inches.

Instead of gauze as the outer wrapping material for making the pad, a cellulose, or synthetic materials having gauze-like properties may be used.

When using unlayered material which is very thin instead of layered material, the folding processes are the same as hereinbefore described except that the material is pre-folded several times to provide the desired thickness.

When cutting the material, the type of cut can be pressed cut with some pinking so as to minimize the fraying at the cut edges.

Instead of using zig-zag stitching for the different forms, as hereinbefore described, straight chain stitching, or other types of known stitching may be used to hold the outer covering together at their ends to create the leading edges and leading edge panels also hereinbefore described.

It will be understood that the dimensions set forth above may be varied to some extent and that the method steps may also be varied, such as the making of the folds by means other than an automatic sequential folding, filling and stitching operation and that when folding is mentioned, it would include rolling of the material to achieve the desired folding.

What is claimed is:

1. A method of making feminine hygienic pads from a material of predetermined width with opposed longitudinal edges and opposed faces by folding said material into longitudinal folds providing a folded form; the method including inwardly folding one longitudinal edge over one face of the material to provide a fold formed anterior leading edge with a first panel, inwardly folding the other longitudinal edge over said one face to provide a folded second edge with a second panel, inwardly folding the folded second edge with its panel over said one face across a major portion of the width of the material and over the inwardly folded first panel to a point short of the anterior leading edge, and stitching the inwardly folded second edge to the underlying mterial inward of the anterior leading edge to define a narrow anterior portion and a relatively wider posterior portion relative to the stitching.

2. The method as in claim 1 including the insertion of a filler material between the folds and prior to stitching.

3. The method as in claim 1 including cutting the folded and stitched material transverse to the folds to define predetermined length pads.

4. A method of making feminine hygienic pads from a material of predetermined width with opposed longitudinal edge portions and opposed faces by folding said material into longitudinal folds providing a folded form; the method including forming a first panel by one or more inwardly directed folds of one longitudinal edge portion over one face of the material to provide a fold formed anterior leading edge, forming a second panel by one or more inwardly directed folds of the other longitudinal edge portion over said one face, and folding the second panel across a major portion of the width of the one face, and over the first panel to a point short of the anterior leading edge formed during the folding of the first panel, and stitching the forward folded edge of the second panel to the underlying material inwardly of the anterior leading edge formed by the folding of the first panel to define a narrow anterior portion and relatively wider posterior portion relative to the stitching.

5. The method as in claim 4 including the insertion of a filler material between the folds and prior to stitching.

6. The method as in claim 4 including cutting the folded and stitched material transverse to the folds to define predetermined length pads.

7. The method of making feminine hygienic pads from a material of predetermined width with opposed exposed free edges and opposed faces by folding the material into longitudinal folds providing a folded form; the method including inwardly folding the opposed edge portions of the materials to present folded anterior and posterior edges, and inwardly folding one of said folded edges across a major portion of the width of the material to a point short of the other folded edge so as to conceal both exposed free edges, and stitching the inwardly folded one of said folded edges to the underlying material and inward of the other folded edge to define a narrow anterior portion with an anterior leading edge and relatively wider posterior portion relative to the stitching.

8. The method as in claim 7 including the insertion of a filler material between the folds and prior to the stitching.

9. The method as in claim 7 including cutting the folded and stitched material transverse to the folds to define predetermined length pads.

10. A method of making feminine hygienic pads of material of predetermined width with opposed exposed free edges and opposed faces by folding the material into longitudinal folds providing a folded form, the method including inwardly folding one longitudinal edge of the material over one face of the material one or more times to provide a fold formed anterior leading edge with a first panel, inwardly folding the other exposed free edge across a major portion of the width of the material to a point short of the anterior leading edge, stitching the free edge to the underlying material and inward of the anterior leading edge to define a narrow anterior portion and a relatively wider posterior portion relative to the stitching.

11. The method as in claim 10 including the insertion of a filler material between the folds and prior to the stitching.

12. The method as in claim 10 including cutting the folded and stitched material transverse to the folds to define predetermined length pads.

13. The method as in claim 2 including cutting the folded, filled and stitched material transverse to the folds to define predetermined length pads.

14. The method as in claim 5 including cutting the folded, filled and stitched material transverse to the folds to define predetermined length pads.

15. The method as in claim 8 including cutting the folded, filled and stitched material transverse to the folds to define predetermined length pads.

16. The method as in claim 11 including cutting the folded, filled and stitched material transverse to the folds to define predetermined length pads.

* * * * *